United States Patent [19]

Schwartz

[11] Patent Number: 5,139,500
[45] Date of Patent: Aug. 18, 1992

[54] BONE ATTACHMENT SYSTEM

[76] Inventor: Nathan H. Schwartz, 7 Heards Overlook Ct., Atlanta, Ga. 30328

[21] Appl. No.: 462,588

[22] Filed: Jan. 9, 1990

Related U.S. Application Data

[63] Continuation-in-part of Ser. No. 348,516, May 8, 1989, abandoned.

[51] Int. Cl.⁵ .................................................. A61F 5/04
[52] U.S. Cl. ........................................ 606/96; 606/98; 606/103
[58] Field of Search ...................... 606/56, 57, 60, 62, 606/64, 65, 66, 67, 72, 75, 96, 97, 98, 102, 103, 104, 59; 623/17

[56] References Cited

U.S. PATENT DOCUMENTS

| | | | |
|---|---|---|---|
| 2,143,922 | 1/1939 | Longfellow | 606/59 |
| 2,697,433 | 12/1954 | Zehnder | 606/103 |
| 3,727,610 | 4/1973 | Riniker | 606/59 |
| 4,050,528 | 9/1977 | Foltz | 606/104 |
| 4,091,880 | 5/1978 | Troutner | 606/104 |
| 4,342,309 | 8/1982 | Eftekhar | 606/104 |
| 4,360,012 | 11/1982 | McHarrie | 606/59 |
| 4,624,249 | 11/1986 | Cambras | 606/59 |
| 4,869,242 | 9/1989 | Galluzzo | 606/59 |
| 4,878,915 | 11/1989 | Brantigan | 623/17 |
| 4,920,958 | 5/1990 | Walt | 606/103 |

Primary Examiner—Robert A. Hafer
Assistant Examiner—Michael Brown
Attorney, Agent, or Firm—B. J. Powell

[57] ABSTRACT

An attachment wire construction for attaching bone together, including an elongated wire having a leading end defining a drill tip. The wire has an anular breakneck groove that forms a reduced diameter frangible section. The leading end of the wire is externally threaded along the length of the wire.

19 Claims, 5 Drawing Sheets

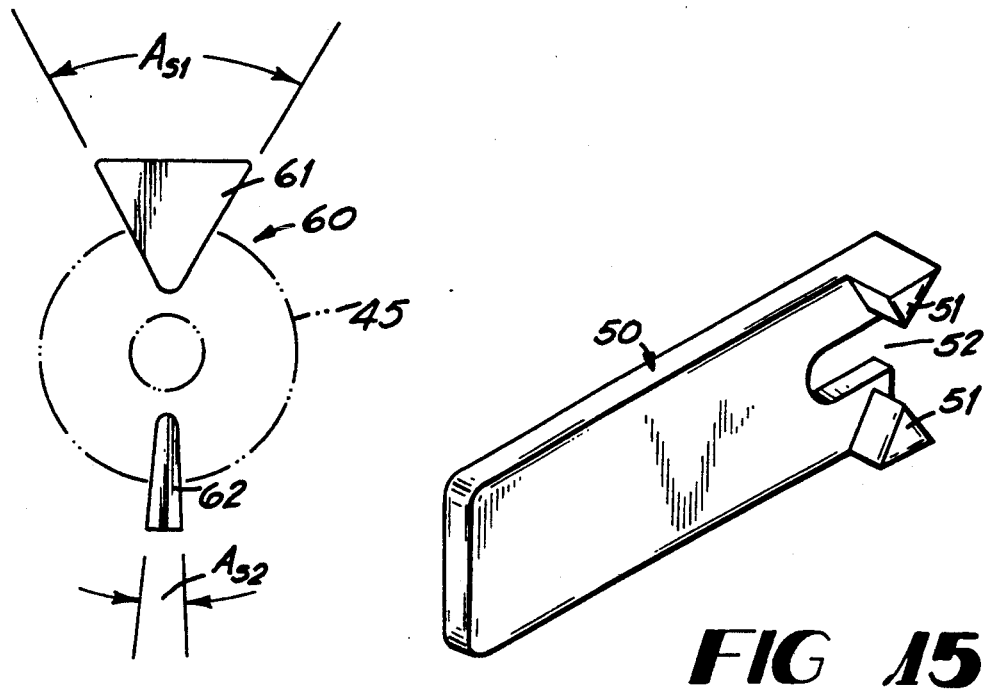
FIG 17
FIG 15
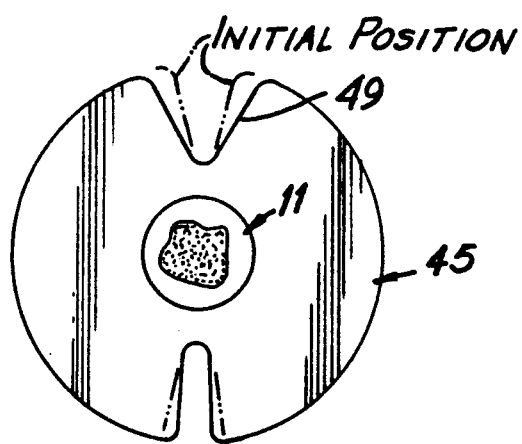
FIG 18

BONE ATTACHMENT SYSTEM

CROSS REFERENCE TO RELATED APPLICATIONS

This application is continuation-in-part of my co-pending application Ser. No. 07/348,516, filed May 8, 1989, now abandoned.

BACKGROUND OF THE INVENTION

This invention relates generally to techniques for attaching bones together and more particularly to techniques using threaded members to attach bones together.

It is frequently necessary to hold fractured or surgically cut bones together until they are healed. While many broken bones are supported externally with casts, splints and the like, it is a common practice to support bones internally using threaded fastening devices. One such fastening device is a threaded wire commonly known as a K-wire or Kirschner wire. Such threaded wires have a sharpened point on at least one end thereof so that the wire drills into the bone as it is rotated with appropriate driving tools while at the same time cutting threads in the bone so that the threads following the sharpened tip can threadedly engage the bone to hold it in position.

One of the problems with such K-wires is that it is difficult to accurately locate the drill point on the K-wire to start penetration of the bone, a relative large incision must be made to gain access to the site and to the path along which the K-wire passes through the tissue around the bone, and a relative large incision is necessary to cut the wire off with a cutting implement after it is installed. Also it is difficult to tell how far in the bone the wire has penetrated. It is also difficult to use the K-wire to increase the clamping force on the fracture or cut over the initial clamp up force applied before the K-wire is installed. As a result using the prior art K-wires has been a tedious and time-consuming operation. Also, the requirement that larger incisions be made resulted in a greater likelihood of infection.

SUMMARY OF THE INVENTION

These and other problems and disadvantages associated with the prior art are overcome by the invention disclosed herein by providing a bone attachment system which permits a threaded wire to be installed across the fracture or cut using only a small incision, which permits the wire to accurately located, and which allows the wire to be separated at the bone surface with minimum tissue damage around the installation site. The threaded wire used in the system is provided with an annular breakneck groove at a prescribed location along the length thereof so that the attachment wire remains sufficiently strong in tension to prevent separation of the wire during installation but sufficiently weak at the breakneck groove to permit the wire to be fractured by bending the wire sidewise. A wire guide is provided to penetrate the tissue at the installation site without the typically large incision previously required. The guide also acts to locate the drill point on the wire and as a shield to prevent the wire from winding the tissue around it as it is screwed into the bone. At the same time the guide can be rotated so as to allow the wire to be viewed at the bone surface so that the breakneck groove can be visually aligned with the bone surface and then broken off with trauma to the tissue around the installation site. As a result, the incision required to install the wire is minimized. After the wire is installed up to the breakneck groove (the location of the breakneck groove is indicated by a marking on the wire itself), the surgeon simply bends the wire to the side to snap the wire flush with or slightly below the bone surface.

These and other features and advantages of the invention will become more clearly understood upon consideration of the follow detailed description and accompanying drawings wherein like characters of reference designate corresponding parts throughout the several views and in which:

BRIEF DESCRIPTION OF THE DRAWINGS

FIG. 15 is a perspective view illustrating an installation tool to install the nut;

FIG. 17 is a view schematically illustrating the swaging operation; and

FIG. 18 is a face view of the nut swaged onto the attachment wire.

These figures and the following detailed description disclose specific embodiments of the invention, however, it is to be understood that the inventive concept is not limited thereto since it may be embodied in other forms.

DETAIL DESCRIPTION OF ILLUSTRATIVE EMBODIMENTS

Figure 1:
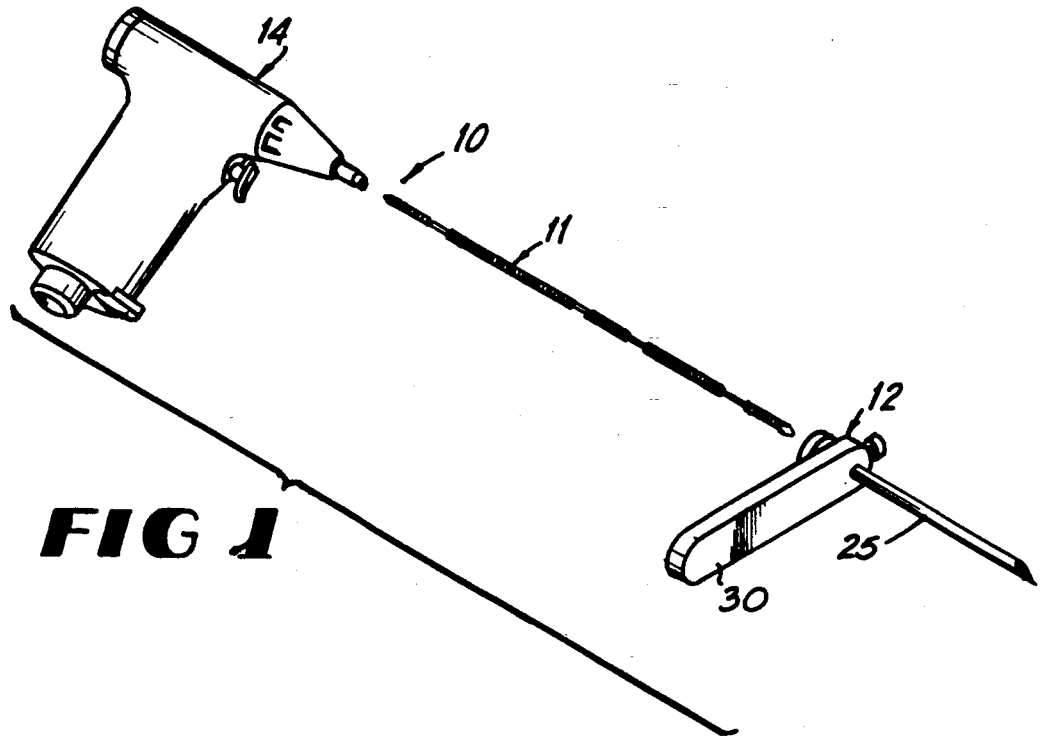
FIG. 1 is an exploded perspective view showing first embodiment of the system of the invention.

Referring to FIG. 1, it will be seen that the apparatus 10 used in the invention includes a threaded attachment wire 11, a guide 12 and a driving tool 14. The guide 12 is used to guide the attachment wire 11 through and isolate the wire from the patient's flesh around the fractured or cut bone B as it is being installed. After the wire 11 is installed and broken off as will become more apparent, that portion of the wire remaining in the bone serves to hold the break or cut in the bone together until it heals.

Figure 2:
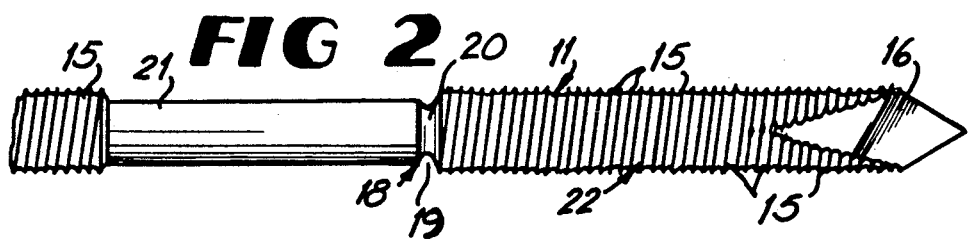
FIG. 2 is an enlarged side view of the end of an attachment wire used in the invention.
Figure 3:
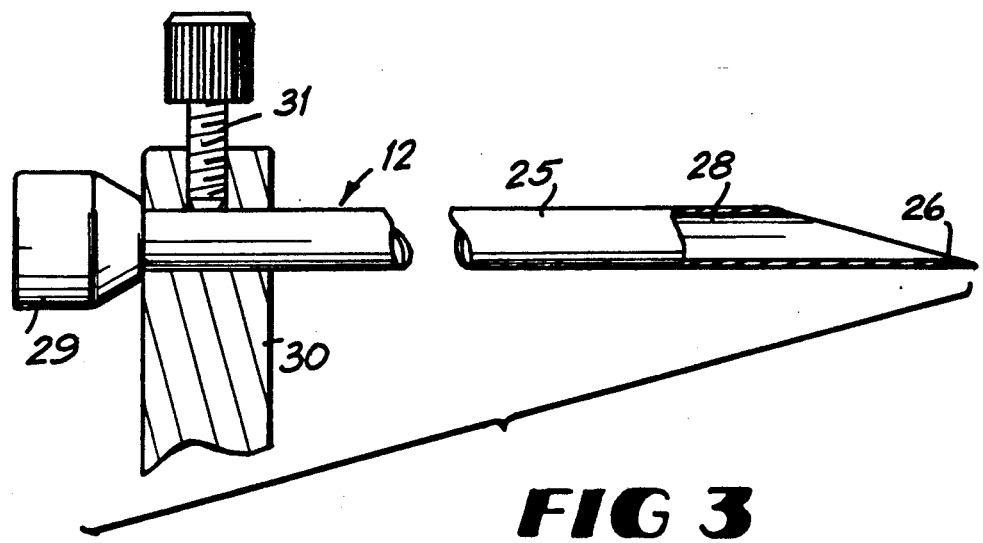
FIG. 3 is an enlarged view shown partly in cross-section of the wire guide used in the system of the invention.

Referring to FIG. 2, it will be seen that the attachment wire 11 is externally threaded as indicated at 15 along its length. Opposite ends of the wire 11 are cut into sharpened drill points 16 as is typical of K-wires so that the point 16 can be used to drill into the bone B into which the wire 11 is being installed as will become more apparent. Each end of the wire 10 is provided with a breakneck section 18 spaced a prescribed distance d from the end of the wire 11.

Each drill point 16 has multiple planar surface that taper inwardly form a sharpened point at the projecting most end of the wire as it typical for K-wires. Because the threads 15 run into the edges of the planar surfaces on the wire, theses threads serve to cut the threads in the bone for the trailing thread on the wire.

Each breakneck section 18 includes an annular breakneck groove 19 cut into the wire 11 a distance d from the tip of the drill point on the wire 11. The remaining frangible portion 20 of the wire 11 at groove 19 is thus weaker than the main body of the wire and the wire is sufficiently hardened to cause the section 20 to snap thereat when the wire 11 is laterally flexed. Thus, the distance d is selected to correspond to the distance of penetration of wire 11 into the bone and the wire is installed in the bone up to the section 18 as will become more apparent. Because the breakneck groove 19 extends completely around the wire 11, a smooth fracture is made in the frangible portion 20.

To mark the location of the breakneck section 18, a contrasting marking 21 is provided on that side of the breakneck groove 19 opposite the working section 22 containing the drill tip 16. This location of the marking 21 allows it to remain visible to the surgeon installing the same when the working section 22 is fully installed. The marking 21 may have any convenient form and is shown as an unthreaded section with an outside diameter sightly smaller than the root diameter of the threads 15 so that the section 21 will not damage the threads tapped into the bone by the threaded portion of the tip 16 as the wire 11 is driven into position. The marking 21 is required because the surgeon has great difficulty seeing the breakneck groove 19 while the wire 11 is being installed.

Because the wire 11 needs to be installed as near perpendicular to the fracture or cut in the bone as possible, the angle with the axis of the bone at which the wire is installed varies from application to application. Many times this included angle needs to be as acute as possible. An incision is usually made through the tissue surrounding the bone at the point where the point of the drill tip 16 is to penetrate the bone. To allow the angle between the bone and wire to be acute, the point of the drill tip 16 needs to penetrate the skin at a position spaced a significant distance axially of the bone from the point of entry into the bone.

The guide 12 serves to permit the skin to be penetrated percutaneously away from the incision at the point of entry into the bone without having to make an incision large enough to open both points of entry to allow the angle between the bone and wire to be more acute. The guide 12 includes a trocar 25 which has an angled sharpened needle tip 26 that makes a slit in the skin as it penetrates the same rather than cutting a round plug out of the skin. The diameter of the passage 28 through the trocar 25 is sufficient to just clear the wire 11 as it passes through the trocar 25. Because the tip 26 makes a slit, the surgeon can orient the tip 26 so that the slit in skin will be oriented parallel to the orientation of the tensile stress in the skin to minimize the opening of the slit made by the trocar 25. A hub 29 is normally on that end of the trocar 25 opposite the tip 26.

The guide 12 also includes a handle 30 with a hole through one end to receive the trocar 25 therethrough so that the trocar is oriented normal to the handle axis. A locking screw 31 is provided that threadedly engages the handle 30 and bears against the trocar to selectively lock the trocar in place both axially and rotationally within the handle 30.

OPERATION

To use the wire 11, the surgeon determines the working length of the wire 11 needed. The working sections 22 will come in different lengths so that the surgeon can select whatever length of working section 22 he needs. Typically, the length d of the working section 22 corresponds to the distance between the point of penetration and the point where the wire would exit the bone on the opposite side of the fracture or cut. It will be appreciated that this distance will be equal to the bone diameter only when the wire 11 is to be installed perpendicular to the bone axis. This distance will typically be considerably more than the bone diameter as will be apparent from FIGS. 5–8.

Figure 4:
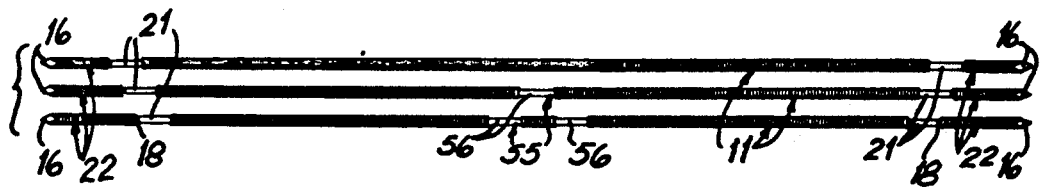
FIG. 4 is an illustration showing the length coding of the attachment wires.

Since different working lengths are required, the wires 11 will be supplied with different lengths d on the working section 22. For the surgeon to distinguish between the various lengths of working sections 22, an encoding arrangement 55 is provided and is best illustrated in FIG. 4. While any number of encodings may be used, the encoding 55 seen in FIG. 4 consist of reduced diameter bands 56 cut in the central portion of the wire 11. While the correspondence between the bands 56 and the lengths d of the sections 22 may be varied as desired, the system illustrated shows no band 56 being used for 10 cm., one band 56 used for 12 cm., two bands 56 used for 14 cm., etc.

Figure 5:
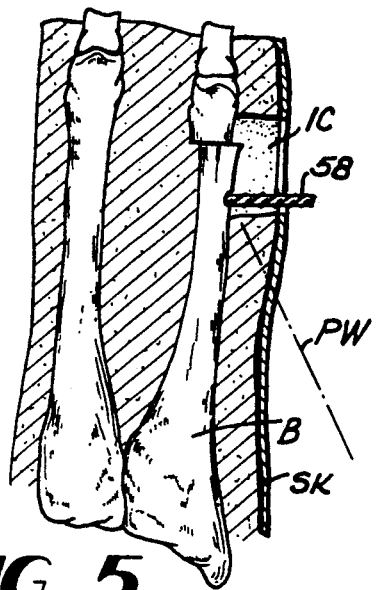
FIGS. 5–9 illustrate the method of the invention.

The invention is illustrate in FIGS. 5–8 being used where a bone repair is being made. In this repair, the bone has shifted out of alignment and, in the surgical procedure, the bone is cut and the end section is being shifted laterally with respect to the bone axis and reattached to straighten same. Either before or after the bone has been cut and shifted as illustrated in FIG. 5, an incision is made to the bone at the point where the wire 11 is to penetrate the bone. Then, a drill 58 is inserted through the incision and used to drill a pilot hole PH in the surface of the bone at that point where the point of the attachment wire 11 is to enter the bone B. The axis of the drill is perpendicular or substantially perpendicular to the bone surface to ease the starting of the drill. Drilling a pilot hole PH serves as a starter hole for the wire 11 as will become more apparent.

Figure 6:
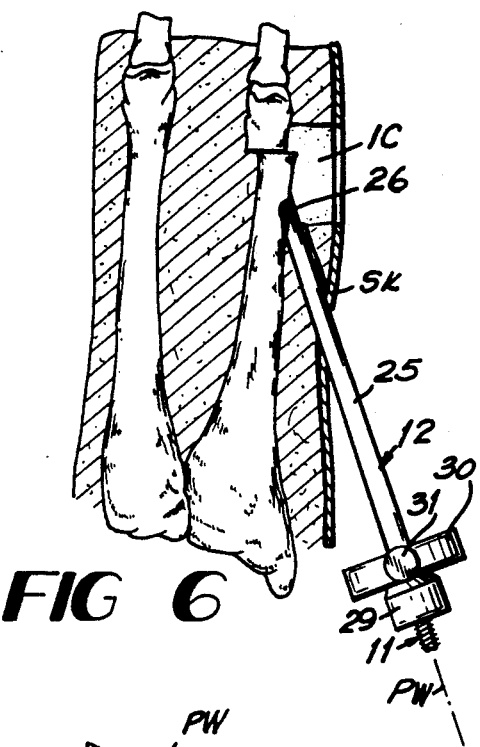
Figure 7:
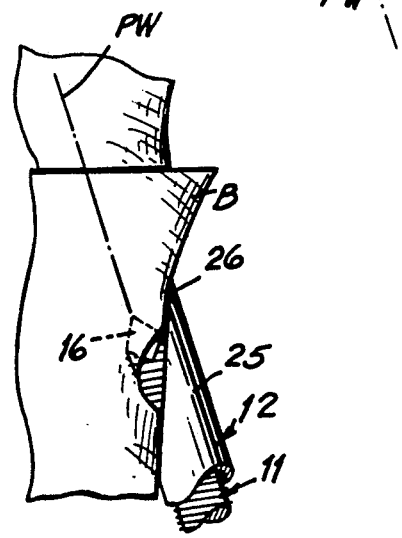

After the pilot hole is formed, the sharpened point 20 on the guide 12 is oriented along the path $P_w$ at which the wire 11 is to be screwed into the bone B and pierces the skin SK so that the tip 26 is in registration with the pilot hole PH in the bone B when the tip 26 seats against the bone as seen in FIG. 6 and 7. The tip 26 is rotated so that the angle of the tip 26 corresponds as closely as possible to the surface of the bone to protect against tissue being caught up in the threads of the wire 11 as it is installed. The orientation of the tip 26 is noted through the incision IC made at the point of entry to the bone for the wire 11. The handle 30 is rotated about the trocar 25 so that the point 26 is properly oriented with respect to the bone and the handle has enough clearance to be operated. The locking screw 31 it tightened down so that the surgeon has control over the trocar 35.

Figure 9:
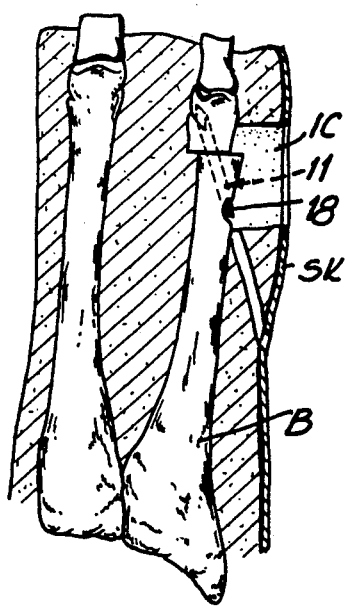
Figure 8:
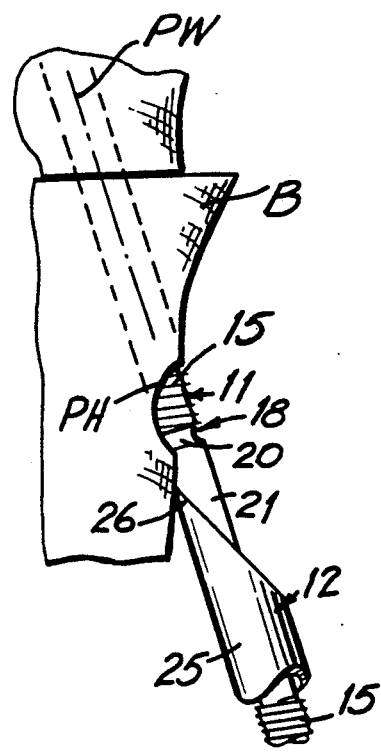

The wire 11 is inserted through the trocar 25 until point 16 engages the pilot hole PH as best seen in FIG. 7. The driving tool 14 is conventional design used with K-wires and is operated conventionally to drive the wire 11 into position. As the surgeon determines that the wire 11 is getting close to its final axial position, the surgeon rotates the trocar 25 180 degrees so that the opening in the tip 26 of the trocar 25 is exposed and the surgeon can easily see the wire 11 passing between the trocar 26 and the bone B as seen in FIG. 8. This allows the surgeon to visually determine when the marking 21 is in registration with the bone surface to determine when the wire 11 is fully seated and is ready to be broken off. Finally, the wire 1 is laterally flexed to cause it to fracture at the breakneck section 20 to separate the working section 22 from the rest of the body of the wire 11. The installed wire 11 is seen in FIG. 9.

COMPRESSION EMBODIMENT

Figure 10:
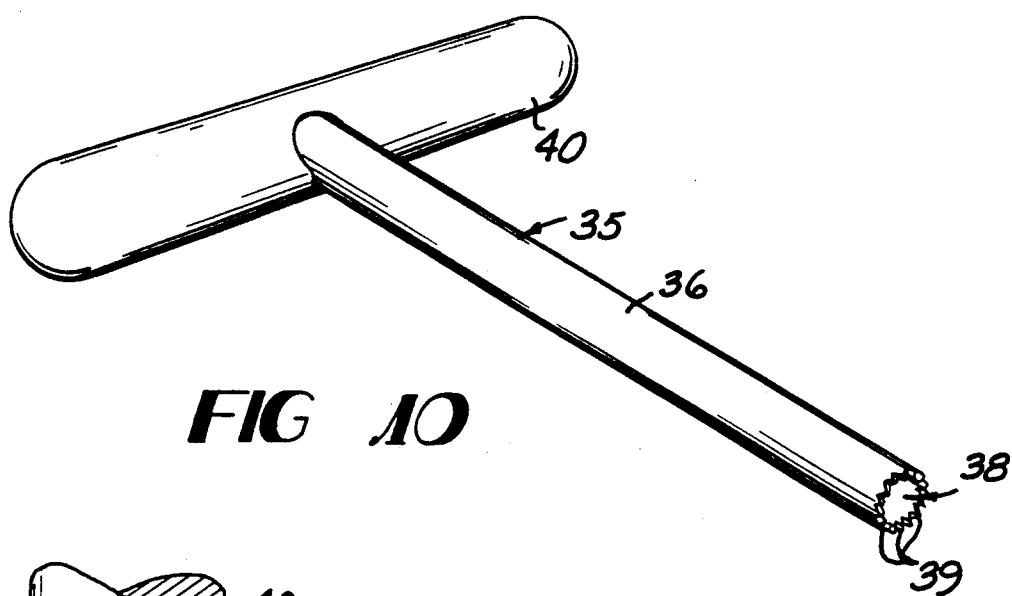
FIG. 10 is perspective view of a trephine used in the installation of a compression nut on the threaded wire.
Figure 11:
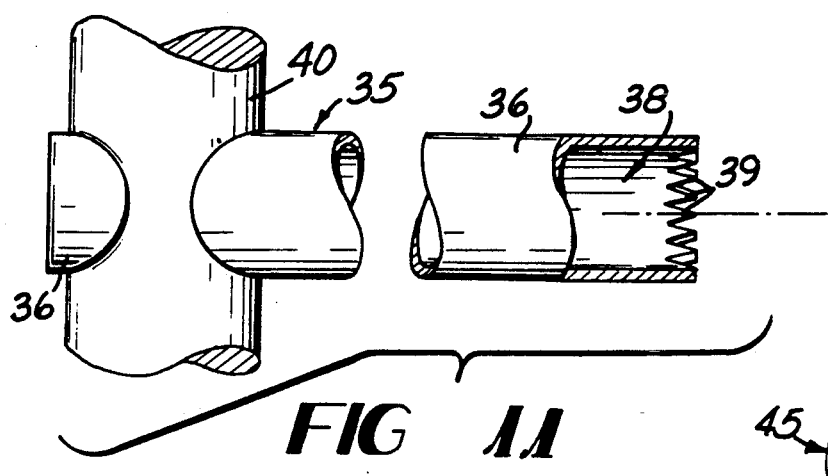
FIG. 11 is an enlarged view shown partly in cross-section of the trephine.
Figure 12:
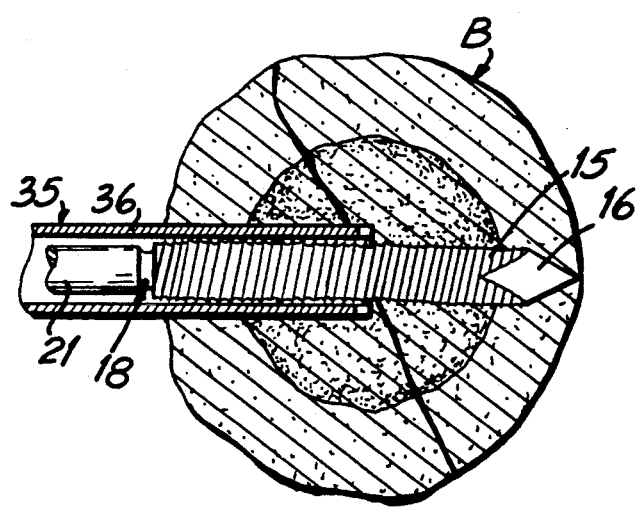
FIG. 12 is a view illustrating the trephine being used.

It is sometimes desirable to provide more compression across the fracture cut in the bone than is available from the initial bone clampup applied independently of the wire 11. The system of the invention also includes a feature whereby additional clampup can be provided as an incident of the installation of the wire 11 in the bone B. FIGS. 10-12 illustrate a trephine 35 which is used to release that portion of the bone on that side of the fracture or cut from which the wire 11 is installed from engagement with the threads 15 thereon. The trephine 35 includes a metal cannula 36 which defines a central passage 38 therethrough just large enough to be received over the threads 15 of the wire 11. The projecting end of the cannula 36 is provided with cutting teeth 39 while the opposite end of the cannula 36 is mounted in a T-handle 40. The trephine 35 is designed so that the wire 11 can pass completely therethrough.

After the wire 11 is installed to the desired depth as described above, the trephine 35 is slipped over the protruding portion of the wire so that the teeth 39 engage the bone around the wire 11 at its entry into the bone. The opposite nd of the wire 11 protruding out of the trephine 35 can be used to hold the wire 11 against turning while the T-handle 40 is rotated to cause the teeth 39 to wear away the hardened portion (cortex) of the bone that grips the thread 15 on the wire 11. This serves to release the near side of the bone from the wire 11. After the bone cortex has been released the trephine 35 is removed. This effectively releases the near side of the bone from the wire 11.

Figure 13:
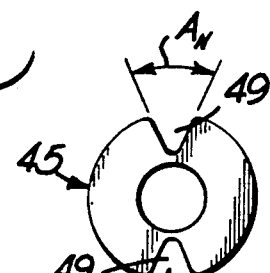
FIG. 13 is a face view of a nut to be installed on the threaded wire.
Figure 14:
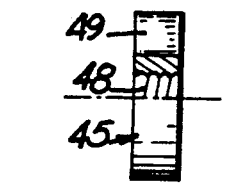
FIG. 14 is a half cross-sectional view of the nut.

To apply pressure across the fracture or cut in the bone B, a nut 45 as best seen in FIGS. 13 and 14 is used. The nut 45 is screwed onto the wire 11 after the trephine 35 is removed so that the nut 45 is carried on the working section 22 of the wire 11. An appropriate washer 46 is placed between the nut 45 and the bone B to act as a bearing surface as the nut 45 is tightened. It will be appreciated that, when the nut 45 is used, a different length working section 22 will be selected. In other words, the additional length corresponding to the nut height and the washer thickness will be added to that corresponding to the bone thickness. Also, the breakneck section 18 is left at a position spaced away from the surface of bone B as seen in FIG. 12 so that enough clearance is provided to engage the nut 45. Typically, the nut 45 is screw onto wire 11 so that the breakneck groove 19 is flush with the projecting side of the nut 45.

The nut 45 illustrated is circular with internal threads 48 adapted to threadedly engage threads 15 on the wire 11. A pair of V-shaped driving notches 49 are provided in the nut 45 at diametrically spaced apart position. An appropriate nut driving tool 50 seen FIG. 15 with drive dogs 51 complementary to the notches 49 and a cutout 52 sized to fit around the wire 11 protruding out of the nut 45 is used to rotate the nut into a position. Usually, the wire 11 is held against rotation while the nut 45 is tightened.

Figure 16:
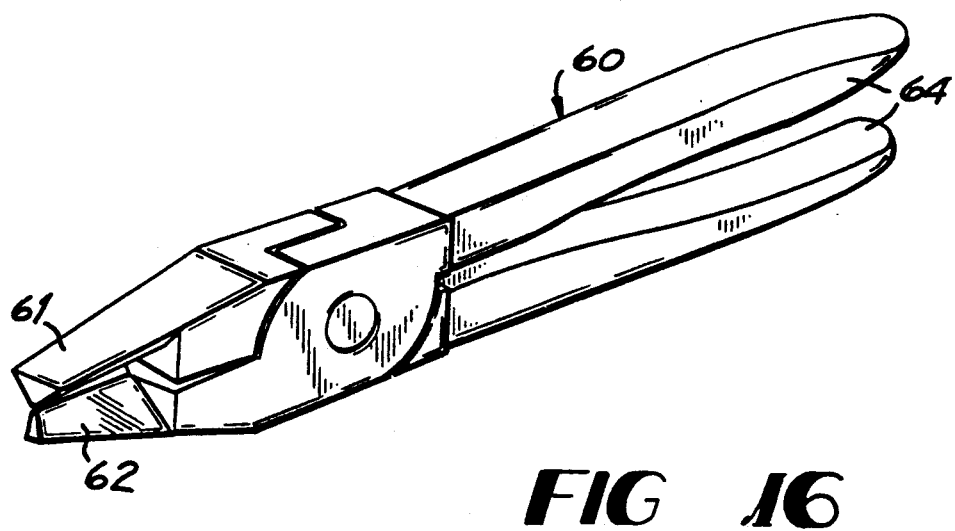
FIG. 16 is a perspective view illustrating an swaging tool to lock the nut onto the attachment wire.

It is typically desirable to lock the nut 45 onto the wire 11 after the nut 45 is finally positioned. This can be accomplished in a number of ways, one of which is distorting at least some of the threads 48 in the nut 45 to get a self-locking feature. To distort the nut 45 after it is in position and the wire 11 broken at the break section 18, a swaging tool 60 is provided as seen in FIG. 16. The nut 45 seen in FIG. 13 in its initial condition defines equal included angles $A_N$ in each of the notches 49. The tool 60 defines at first included angle $A_{S1}$ on its closing anvil 61 and a second included angle $A_{S2}$ on its backup anvil 62 as best seen in FIG. 17. It will be understood that the angle $A_{S1}$ is larger than the notch angle $A_N$ while the angle $A_{S2}$ is the same amount smaller than the notch angle $A_N$. Thus, when the anvils 61 and 62 are positioned in registration with the notches 49 and the handles 64 are closed, the backup anvil 62 will bottom in that notch with which it is in registration while the opening anvil 61 will force the notch 49 with which it is in registration open to distort the nut 45 and thus distort the threads 48 in the nut 45 to lock it onto the threads 15 of the wire 11 as seen in FIG. 18. This serves to lock the nut onto the working section of the wire 11. Once the nut 45 has been locked onto the wire 11, it can be rotated to tighten or loosen the working section 22 of the wire 11 in the bone. Also, the nut 45 can be released from its locked condition by using an appropriate tool (not shown) with anvils which have equal included angles that match the original angles $A_N$ of the notches 49 in the nut 45.

Alternatively, a separate locking member can be forced between the threads 48 in the nut 45 and the threads 15 on the wire 11 after the nut 45 is in position. When the separate locking member is used, the wire 11 is typically not broken at the breakneck section 18 before the lock member is installed.

The use of the locked-on nut 45 greatly facilitates the removal of the working section 22 of the wire 11 left in the bone after the fracture or cut has healed if such removal is warranted or desired. The swaging tool 60 is used to install the nut 45 is simple reinserted into the nut and the nut backed out bringing the working section 22 of the wire 11 therewith.

What is claimed as is:

1. A method of connecting fractured bones together with a threaded attachment wire comprising the steps of:
    a) while maintaining the fractured portion of bone aligned, measuring the thickness of the bone across the fracture along the path at which the attachment wire is to be installed;
    b) selecting an externally threaded attachment wire with a leading end defining a drill trip thereon and defining an annular breakneck groove therearound to form a reduced diameter frangible section in the wire located a distance from the leading end corresponding to the measured bone thickness to define working section between the breakneck groove and the leading end;
    c) using the drill tip on the attachment wire to drill into the bone through the fracture until the breakneck groove is flush with the bone surface so that the threads on the working section engage the bone on both sides of the fracture; and d) laterally moving the projecting portion of the attachment wire to break same at the breakneck groove.

2. The method of claim 1 further comprising the steps of:
   e) prior to step c), piercing the skin and tissue around the bone with the sharpened angled needle tip of a hollow tubular guide member while maintaining the guide member in registration with the installation path along which the attachment wire is to be installed so that the needle tip overlies the point at which the drill tip on the attachment wire is to enter the bone surface;
   f) inserting the attachment wire, drill tip first, through the guide member so that the drill tip engages the bone; and,
   g) holding the guide member in registration with the installation path of the attachment wire while step c) is performed.

3. The method of claim 2 where step g) further includes the substeps of:
   g-1) holding the guide member so that the opening in the sharpened end thereof faces the bone surface until the breakneck groove is in the vicinity of the bone surface; and
   g-2) rotating the guide member so that the opening in the sharpened end thereof faces away from the bone surface so that the breakneck groove is visible for final alignment of the breakneck groove with the bone surface.

4. A method of attaching fractured or cut section of a bone together so that the sections can grow back together against using a threaded attachment wire comprising the steps of:
   a) screwing the attachment wire into both sections of the bone to hold same together with the wire threadedly engaging both sections of the bone and with the wire projecting exteriorly out of one section of the bone;
   b) cutting that section of the bone from which the wire projects closely adjacent to and around the wire to release that section of the bone from engagement with the wire; and,
   c) threadedly engaging that portion of the wire projecting out of the bone with a nut and tightening same to force the sections of the bone together.

5. The method of claim 4 further including the step of:
   d) locking the nut onto the attachment wire so that rotation of the nut serves to rotate the attachment wire.

6. The method of claim 5 wherein step d) includes swaging the nut onto the attachment wire.

7. The method of claim 4 further comprising the steps of:
   d) prior to step a) and while maintaining the fractured sections of bone aligned, measuring the thickness of the bone across the fracture along the path at which the attachment wire to be installed;
   e) still prior to step a), selecting the externally threaded attachment wire with a leading end defining a drill tip thereon and defining an annular breakneck groove therearound to form a reduced diameter frangible section in the wire located a distance from the leading end corresponding to the measured bone thickness to define a working section between the breakneck groove and the leading end;

wherein step a) further includes using the drill tip on the attachment wire to drill into the bone through the fracture until the breakneck groove is located a distance from the bone surface corresponding to the nut thickness so that the threads on the working section engage the bone on both sides of the fracture; and further including:
   f) laterally moving the projecting portion of the attachment wire to break same at the breakneck groove.

8. The method of claim 7 further comprising the steps of:
   e) prior to step a), piercing the skin and tissue around the bone with the sharpened angled needle tip of a hollow tubular guide member while maintaining the guide member in registration with the installation path along which the attachment wire is to be installed so that the needle tip overlies the point at which the drill tip on the attachment wire is to enter the bone surface;
   f) inserting the attachment wire, drill tip first, through the guide member so that the drill tip engages the bone; and,
   g) holding the guide member in registration with the installation path of the attachment wire while step a) is performed.

9. An attachment wire construction for attaching bones together including elongate wire having a leading end defining a drill tip thereon, said wire further defining an annular breakneck groove therearound to form a reduced diameter frangible section in said wire located a prescribed breaking distance from said leading end to define a working section between said breakneck groove and said leading end, said reduced diameter frangible section being smaller in diameter than said working section of said wire, said wire being externally threaded along the length thereof so as to threadedly engage the bone along the total length of said working section.

10. The attachment wire construction of claim 9 wherein said wire includes a visible encoding thereon intermediate each end thereof to indicate the distance between said breakneck groove and the leading end thereof.

11. The attachment wire construction of claim 10 wherein said wire further defines an unthreaded section extending from said breakneck groove away from said leading end to permit said breakneck groove by visually located.

12. The attachment wire construction of claim 11 wherein said unthreaded section has a diameter no greater than a root diameter of the threads on said wire and greater than a minimum diameter of said wire at said breakneck groove.

13. The attachment wire construction of claim 9 further including:
   an internally threaded nut adapted to be screwed onto said external threads on said attachment wire; and
   locking means for selectively locking said nut onto said external threads of said attachment wire.

14. The attachment wire construction of claim 13 wherein said locking means is incorporated in said nut, said nut being deformable after said nut is screwed onto said attachment wire to selectively lock said nut onto said external threads of said attachment wire.

15. The attachment wire construction of claim 14 wherein said nut defines a pair of opposed, V-shaped driving notches therein; and, further including swaging means for engaging said nut in said notches to selectively deform said nut after said nut is screwed onto said attachment wire to selectively lock said nut onto said external threads of said attachment wire.

16. The attachment wire construction of claim 15 wherein said opposed V-shaped driving notches have an initial common shape and size; and, wherein said swaging means includes means for engaging said notches to open one of said notches further and to close one of the notches down from its original size to distort the threads in said nut and lock said nut onto said attachment wire.

17. The attachment wire construction of claim 16 further including removal means for selectively engaging said nut in said notches after said notches have been distorted to reform said notches back to their original shape so that said nut is released to be unscrewed off said attachment wire.

18. A bone attachment system for attaching fractured or cut sections of a bone together so that the sections can grow back together again comprising:

an elongate externally threaded attachment wire having a leading end defining a drill tip thereon adapted to drill and self-tap into both sections of the bone to hold same together with the wire threadedly engaging both sections of the bone; and a tubular guide member defining a projecting end thereon and a passage therethrough sized to slidably receive the wire therethrough and defining a sharpened angled needle tip on said projecting end adapted to pierce the skin and tissue around the bone along the path at which said wire is to be installed so that the attachment wire can be inserted through the passage in said guide member drill tip first, to protect the skin and tissue wile said attachment wire is being screwed into the bone.

19. A bone attachment system for attaching fractured or cut section of a bone together so that the sections can back together again comprising:

an elongate externally threaded attachment wire having a leading end defining a drill tip thereon adapted to drill and self-tap into both section of the bone to hold same together with the wire threadedly engaging both sections of the bone;

a nut adapted to be screwed onto said attachment wire; and a tubular trephine adapted to slidably fit over said attachment wire and cut the bone from engagement with threads on said attachment wire to release one section of the bone so said nut can then be screwed onto said wire to apply compressive forces across the fracture or cut in the bone.

* * * * *